(12) United States Patent
Ishimaru et al.

(10) Patent No.: US 7,527,720 B2
(45) Date of Patent: May 5, 2009

(54) DEVICE FOR ELECTROPHORESIS, ELECTROPHORESIS EQUIPMENT, ELECTROPHORETIC METHOD, AND SPECIMEN DETECTION METHOD

(75) Inventors: Teruta Ishimaru, Kanagawa (JP); Chiho Itou, Kanagawa (JP); Tadanobu Ikeda, Hiroshima (JP); Takashi Akita, Kanagawa (JP); Osamu Maehara, Kanagawa (JP); Haruko Miyauchi, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 601 days.

(21) Appl. No.: 10/490,118

(22) PCT Filed: Sep. 27, 2002

(86) PCT No.: PCT/JP02/10037

§ 371 (c)(1),
(2), (4) Date: Mar. 26, 2004

(87) PCT Pub. No.: WO03/029820

PCT Pub. Date: Apr. 10, 2003

(65) Prior Publication Data

US 2004/0245103 A1 Dec. 9, 2004

(30) Foreign Application Priority Data

Sep. 28, 2001 (JP) .............................. 2001-300107
Sep. 28, 2001 (JP) .............................. 2001-300108

(51) Int. Cl.
*G01N 27/453* (2006.01)
(52) U.S. Cl. ...................................... 204/605; 204/455
(58) Field of Classification Search ................. 204/605, 204/601, 603, 455, 451

See application file for complete search history.

(56) References Cited

U.S. PATENT DOCUMENTS

| 3,989,612 | A | * | 11/1976 | Kragt et al. | .................. 204/462 |
| 4,217,193 | A | * | 8/1980 | Rilbe | .......................... 204/451 |
| 4,747,918 | A | * | 5/1988 | Wassenberg, II | ............ 204/462 |
| 4,994,161 | A | * | 2/1991 | Laue et al. | ................... 204/450 |
| 5,366,608 | A | * | 11/1994 | Kambara | ..................... 204/603 |
| 6,093,370 | A | * | 7/2000 | Yasuda et al. | ............... 422/68.1 |
| 6,183,970 | B1 | * | 2/2001 | Okano et al. | .................... 435/6 |

(Continued)

FOREIGN PATENT DOCUMENTS

JP          9-504864          5/1997

(Continued)

OTHER PUBLICATIONS

U.S. Appl. No. 11/514,162, filed Sep. 1, 2006, Akita et al.

*Primary Examiner*—Kaj K Olsen
(74) *Attorney, Agent, or Firm*—Oblon, Spivak, McClelland, Maier & Neustadt, P.C.

(57) ABSTRACT

An electrophoretic device in the form of a casing having inside sealed spaces isolated by an electrophoretic carrier. The device includes at least one liquid injection/discharge opening, communicable with the outside, on the outer wall of said sealed spaces. An electrophoretic method and a specimen detection method use the device. Additionally, an electrophoresis apparatus can have a structure for sandwiching the electrophoretic carrier between a pair of electrodes, and can have a space capable of holding liquid between the sandwiched electrophoretic carrier and the respective electrodes, and an electrophoretic method uses the same device.

5 Claims, 14 Drawing Sheets

U.S. PATENT DOCUMENTS

| | | | |
|---|---|---|---|
| 7,122,378 B1 * | 10/2006 | Akita et al. | 436/94 |
| 2004/0245103 A1 | 12/2004 | Ishimaru et al. | |

FOREIGN PATENT DOCUMENTS

| | | |
|---|---|---|
| JP | 11-127900 | 5/1999 |
| JP | 2000-342298 | 12/2000 |
| JP | 2001-83158 | 3/2001 |
| JP | 2001-161361 | 6/2001 |
| JP | 2001-255328 | 9/2001 |

* cited by examiner 11   12   13

DEVICE FOR ELECTROPHORESIS, ELECTROPHORESIS EQUIPMENT, ELECTROPHORETIC METHOD, AND SPECIMEN DETECTION METHOD

CROSS-REFERENCE TO RELATED APPLICATIONS

The present application is the United States national stage application of International Application No. PCT/JP02/10037 and claims priority to Japanese Patent Application No. 2001-300107 and No. 2001-300108.

TECHNICAL FIELD

The present invention relates to an electrophoretic device, an electrophoresis apparatus, an electrophoretic method, and a specimen detection method for detecting bio-related substances including nucleic acids, proteins, polypeptides and polysaccharides.

BACKGROUND ART

These years have seen the advent of the use of the chips referred to as biochips (DNA chips and the like), for the purposes of diagnosing diseases and elucidating the causes thereof, in which the probes for bio-related substances such as nucleic acids are arranged on a plane in a manner partitioned into respective different types of probes, namely, in many spots respectively immobilizing different types of probes.

For biochips, known are a method for immobilizing nucleic acids by spotting on a substrate modified chemically or physically (Science 270, 467 to 470 (1995)), and methods in which short chain nucleic acids are solid-phase synthesized directly on a silicon substrate or the like with the aid of photographic techniques (U.S. Pat. No. 5,445,934, U.S. Pat. No. 5,774,305). The spotting method suffers from a large variation from spot to spot in the amounts of the nucleic acids immobilized on the spots, so that the reproducibility from chip to chip is poor, and hence it is very difficult to produce uniform chips in quantity. The photography method is small in the variation from spot to spot in the amounts of nucleic acids immobilized on the spots and accordingly excellent in the reproducibility over a set of chips; however, the expensive manufacturing apparatus and the multistep manufacturing processes make the chips expensive, and additionally, the syntheses of nucleic acids are made on the substrate such that the syntheses of long chain nucleic acids have been difficult.

In this connection, nowadays biochips with a gel containing the immobilized probes for the bio-related substances such as nucleic acids have attracted attention which are small in the variation of the amounts of the nucleic acids immobilized on the respective spots, excellent in the reproducibility from chip to chip, independent of the nucleic acid chain lengths, and easily immobilizable to the substrate (JP Patent Publication (Kokai) No. 2000-270878, JP Patent Publication (Kokai) No. 2000-60554). In particular, the biochip disclosed in JP Patent Publication (Kokai) No. 2000-270878 is a slice obtained by cutting, along a sectional plane intersecting the fiber axis, a fiber assembly (3-dimensional array) of a plurality of hollow fibers regularly arranged and holding a bio-related substance immobilized gel which each contains a different types of bio-related substances such as a variety of nucleic acids (hereinafter referred to as a capillary array sheet). It is greatly expected in the market as an inexpensive and mass-producible biochip.

In such biochips in which probes for bio-related substances such as nucleic acids are immobilized in a gel, bio-related substance specimens such as nucleic acids in an electrolyte are made to migrate into the gel by electrophoresis, so that the probes of bio-related substances and the bio-related substance specimens are hybridized efficiently, and furthermore, the non-hybridized, unnecessary specimens can be washed out. A description of electrophoresis on the DNA chip is found in JP Patent Publication (Kokai) No. 2000-60554, which involves an electrophoretic method using a chip equipped with electrodes, and hence cannot be applied to the above described capillary array sheet. On the other hand, arranging electrodes on the chip for the purpose of conducting electrophoresis unpreferably leads to cost rising.

DISCLOSURE OF THE INVENTION

Figure 1:
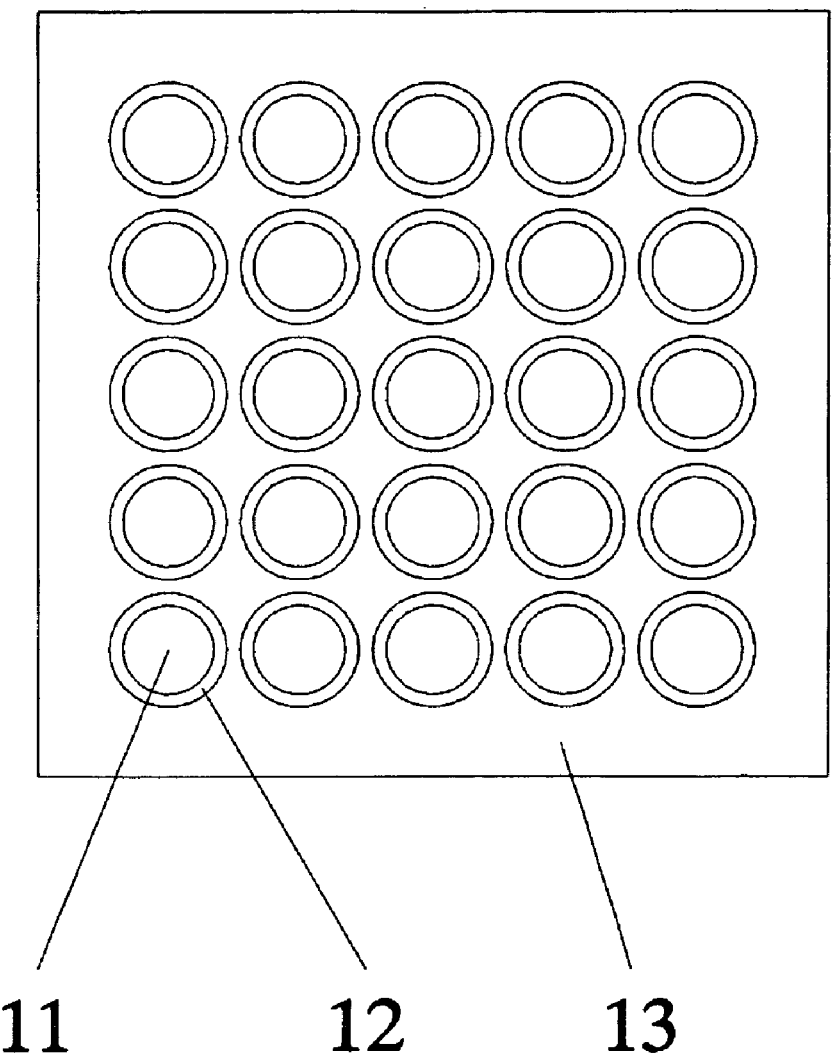
FIG. 1 is a schematic diagram illustrating the surface of a capillary array sheet.

A capillary array sheets are characterized in that these sheets can be mass produced at a low cost. The present invention particularly takes as its objects to provide an electrophoretic device, an electrophoresis apparatus, an electrophoretic method and a specimen detection method, suitable for the capillary array sheet.

The chips are preferably stored in casings to prevent contamination of and maintain the quality of the chips during storage and transportation, and furthermore the chips in which probes of bio-related substances are immobilized in a gel are preferably stored in a liquid so that the gel may not be dried.

For the purpose of efficiently conducting hybridization between the specimens and the probes immobilized in the gel and washing the unnecessary specimens, the temperature can be preferably controlled. Furthermore, when various types and sizes of nucleic acids are subject to electrophoresis as specimens, the electrophoresis behaviors of the respective nucleic acids are different from each other, so that if the electrophoresis conditions of the nucleic acids can be monitored in real time, the hybridization reaction and the washing and removing of the unnecessary specimens can be performed without fail.

The object of the present invention includes the solution of these problems.

As a result of the diligent investigation for the purpose of overcoming the above described problems, the present inventors have discovered that there can be provided an electrophoretic device, as well as an electrophoretic method and a specimen detection method using the same device, for detecting bio-related substances including nucleic acids, proteins, polypeptides and polysaccharides, which is inexpensive, mass producible, and excellent in storagibility, by housing an electrophoretic carrier such as capillary array sheet or the like in a casing in which electrophoresis, hybridization, washing and detection can be carried out.

Additionally, the present inventors have discovered that there can be provided an electrophoresis apparatus and an electrophoretic method both compatible with capillary array sheet and the like as an electrophoretic carrier.

Specifically, the present invention is an electrophoretic device in the form of a casing having a sealed space isolated by the electrophoretic carrier in the interior thereof, characterized in that the device has, on the outer wall of the sealed space, at least one liquid injection/discharge opening communicable with the outside. Preferably, the present invention is an electrophoretic device in the form of a casing having two sealed spaces isolated by the electrophoretic carrier in the interior thereof, characterized in that the device has, on the outer wall of each of the two sealed spaces, at least one liquid injection/discharge opening communicable with the outside. As the electrophoretic carrier, preferable is a capillary array sheet in which a polymer gel immobilizing the probes is held in the hollow portions of the capillaries. Additionally, the casing is formed of, for example, a transparent material.

Additionally, the present invention is an electrophoretic method characterized in that a specimen solution and an electrolyte are each injected, through the liquid injection/discharge opening, into the isolated sealed space in the interior of the casing of the above described electrophoresis apparatus, and thereafter electrodes are inserted through the liquid injection/discharge openings into the isolated sealed space and a voltage is applied to make the specimen molecules migrate into the electrophoretic carrier. The specimen solution and the electrolyte are injected, for example, through injectors, and the injectors can be used as the electrodes. Preferably, the present invention is an electrophoretic method in which a specimen solution and an electrolyte are each injected, through the liquid injection/discharge openings, in the two isolated sealed spaces in the interior of the casing of the above described electrophoresis apparatus, and thereafter electrodes are inserted through the liquid injection/discharge openings respectively into the two isolated sealed spaces and a voltage is applied to make the specimen molecules migrate into the electrophoretic carrier.

Additionally, the present invention is an electrophoretic method characterized in that conductive liquid injectors/dischargers are inserted, through the liquid injection/discharge openings, in the isolated sealed space in the interior of the casing of the above described electrophoresis apparatus, and thereafter while a washing solution is injected into and discharged from the isolated sealed space, a voltage is applied between the liquid injectors/dischargers and the unnecessary specimen molecules are made to migrate and removed from the surface and the interior of the electrophoretic carrier. Preferably, the present invention is an electrophoretic method characterized in that conductive liquid injector/discharger is inserted, through the at least one liquid injection/discharge opening, in each of the two isolated sealed spaces into the interior of the casing of the above described electrophoresis apparatus, and thereafter while a washing solution is injected into and discharged from each of the two isolated sealed space, a voltage is applied between the liquid injectors/dischargers and the unnecessary specimen molecules are made to migrate and removed from the surface and the interior of the electrophoretic carrier.

Additionally, the present invention is a detection method characterized in that in the above described electrophoretic methods, light is irradiated perpendicularly onto the surface of the electrophoretic carrier to detect the specimen molecules on the surface and interior of the electrophoretic carrier. The detection of the specimen molecules can be conducted by detecting the fluorescence from the fluorescent molecules bonded to the specimen molecules.

Additionally, the present invention is an electrophoresis apparatus characterized in that the aparatus has a structure in which a pair of electrodes sandwich the electrophoretic carrier, and there are spaces, capable of holding liquid, between the sandwiched electrophoretic carrier and the respective electrodes. As the electrophoretic carrier, preferable is a capillary array sheet holding the polymer gel having probes immobilized thereto in the hollow portions of the capillaries. The space capable of holding liquid is formed of, for example, a horseshoe-shaped portion on the electrode. Additionally, a structure in which a biochip is sandwiched by a pair of electrodes, can be adopted such that one electrode of the pair of electrodes can be movable in a manner facing the other electrode. Examples of the electrode include an electrode which has at least one liquid injection/discharge opening communicable with a space capable of holding liquid or a light transmission window. Additionally, the electrode can be made to be temperature controllable.

Additionally, the present invention is an electrophoretic method in which electrophoresis is conducted while optically detecting the specimens by using an electrophoresis apparatus having a light transmission window on an electrode thereof.

Description will be made below on an embodiment of the present invention with reference to the accompanying drawings by exemplifying, as the electrophoretic carrier, a capillary array sheet using hollow fibers. However, the electrophoretic carrier is not limited to the above described capillary array sheet.

FIG. 1 is a schematic diagram illustrating the surface of a capillary array sheet. Reference numeral 11 denotes a polymer gel made of acrylamide, agarose and the like immobilizing probes for bio-related substances such as nucleic acids, proteins and the like (hereinafter referred to as probes), reference numeral 12 denotes a hollow fiber holding the gel 11, and reference numeral 13 denotes a matrix adhering the hollow fibers 12. FIG. 1 exemplifies a capillary array sheet which is an electrophoretic carrier with the gel immobilizing the probes that are charged in the hollow portions of the hollow fibers; however, this imposes no constraint on the form of the electrophoretic carrier which holds the polymer gel that is the electrophoresis medium. The electrophoretic carrier has only to be a carrier in which the gel immobilizing the probes is charged in a penetrating manner along the thickness direction of the electrophoretic carrier. Examples of the electrophoretic carrier holding a gel other than hollow fiber include an electrophoretic carrier which is formed as follows, as disclosed in JP Patent Publication (Kokai) No. 2000-78998: through-holes are bored in a laminate of a plurality of sheet-like members or block-like members by means of a laser and the like, a gel having probes immobilized thereto is injected into the through-holes, and then the laminate is turned into sheets.

Figure 2:
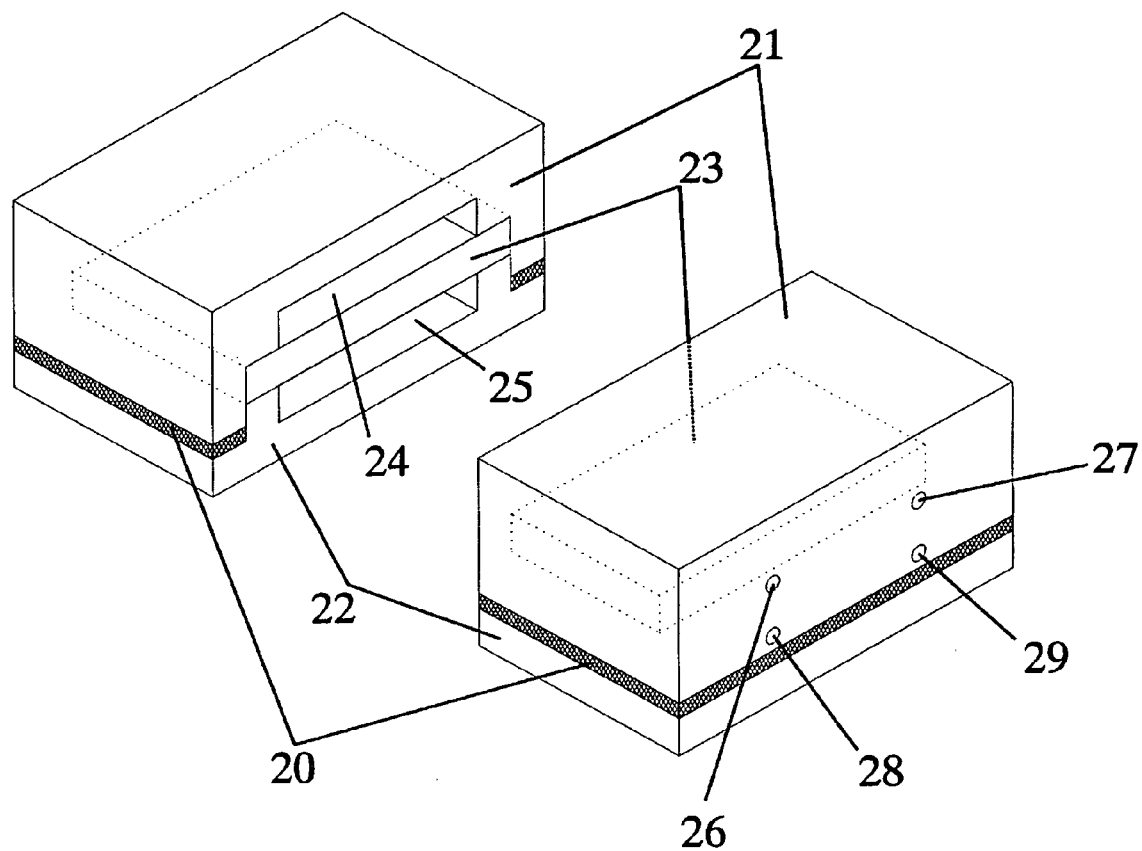
FIG. 2 is a schematic diagram illustrating an electrophoretic device.

FIG. 2 is a schematic diagram illustrating an electrophoretic device, showing that a casing part 21 and a casing part 22 sandwich a capillary array sheet 23, and there are two spaces 24 and 25 isolated by the capillary array sheet 23. Reference numeral 20 denotes an adhesive for bonding the casing part 21 and the casing part 22 together. Reference numerals 26, 27 and 28, 29 are liquid injection/discharge openings each communicated with the spaces 24 and 25 in the interior, and arranged on the casing part 21 and the casing part 22. The thickness of the capillary array sheet falls within the range from a few tens microns to the order of 1 mm. The area sizes usually used are squares of a few mm to a few cm per side. The casing parts 21, 22 can be mass produced at a low price when a plastic material permitting injection molding is used. Additionally, if the casing parts 21, 22 are made of a transparent material such as glass, acrylic resin, transparent electrodes and the like, the condition of the capillary array sheet in the interior of the casing can be observed. Additionally, if the casing is made of a transparent material, fluorescence labeled specimens can be optically detected by irradiating light on the capillary array sheet. When the casing is not made of a transparent material, it is preferable that a window may be arranged and the window portion may be made of a transparent material.

In FIG. 2, a capillary array sheet is used as a packing. Accordingly, two spaces 24 and 25 isolated by a capillary array sheet 23 can be used as a liquid holding space. Additionally, if the capillary array sheet is used as a packing, a capillary array sheet having an arbitrary thickness can be sandwiched between the casing parts 21, 22 both the same as each other in shape. A relatively soft resin is used in the capillary array sheet so that the matrix 13 in FIG. 1 may be easily cut, and hence the embodiment in which the capillary array sheet is used as a packing is suitable for the capillary array sheet.

Figure 3:
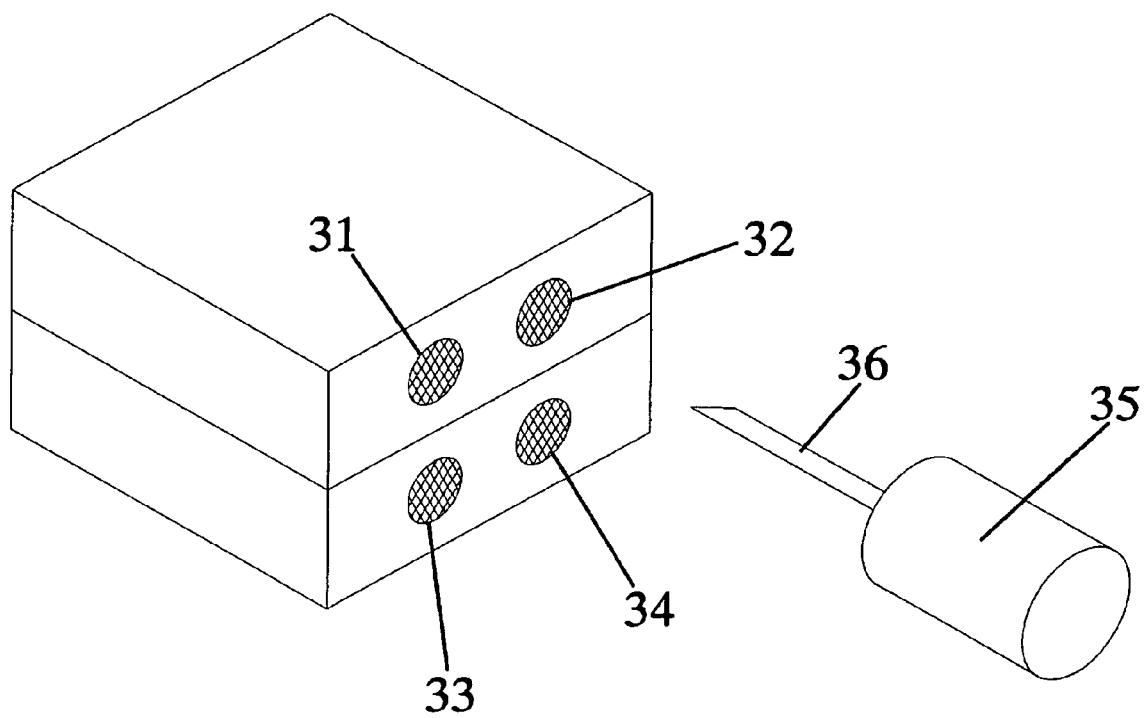
FIG. 3 is a schematic diagram illustrating an electrophoretic device which has liquid injection/discharge openings on the outer wall portion in a manner communicatively connectable with the interior space.

FIG. 3 is a schematic diagram illustrating an electrophoretic device which has liquid injection/discharge openings on the outer wall portion in a manner communicable with the interior space. Reference numerals 31, 32, 33 and 34 denote liquid injection/discharge openings communicable with the interior spaces, more specifically, communicable with the interior spaces isolated by the capillary array sheet. The liquid injection/discharge openings are closed with pieces of soft rubber, film or the like. Reference numeral 35 denotes a liquid injector/discharger and needles 36 for liquid injection/discharge are inserted into the liquid injection/discharge openings to conduct the injection of a specimen solution and the injection and discharge of a washing solution. By use of the conductive needles for liquid injection/discharge 36 subjected to gold plating treatment or the like, and by inserting the needles into the liquid injection/discharge openings 31 and 34 and applying a voltage between the conductive needles at the liquid injection/discharge openings 31 and 34, the specimen molecules can be made to migrate into the gel immobilizing the probes of bio-related substances in the capillary array sheet. Similarly by conducting electrophoresis while similarly injecting and discharging a washing solution, dehybridization, washing and the like can be conducted efficiently.

Figure 4:
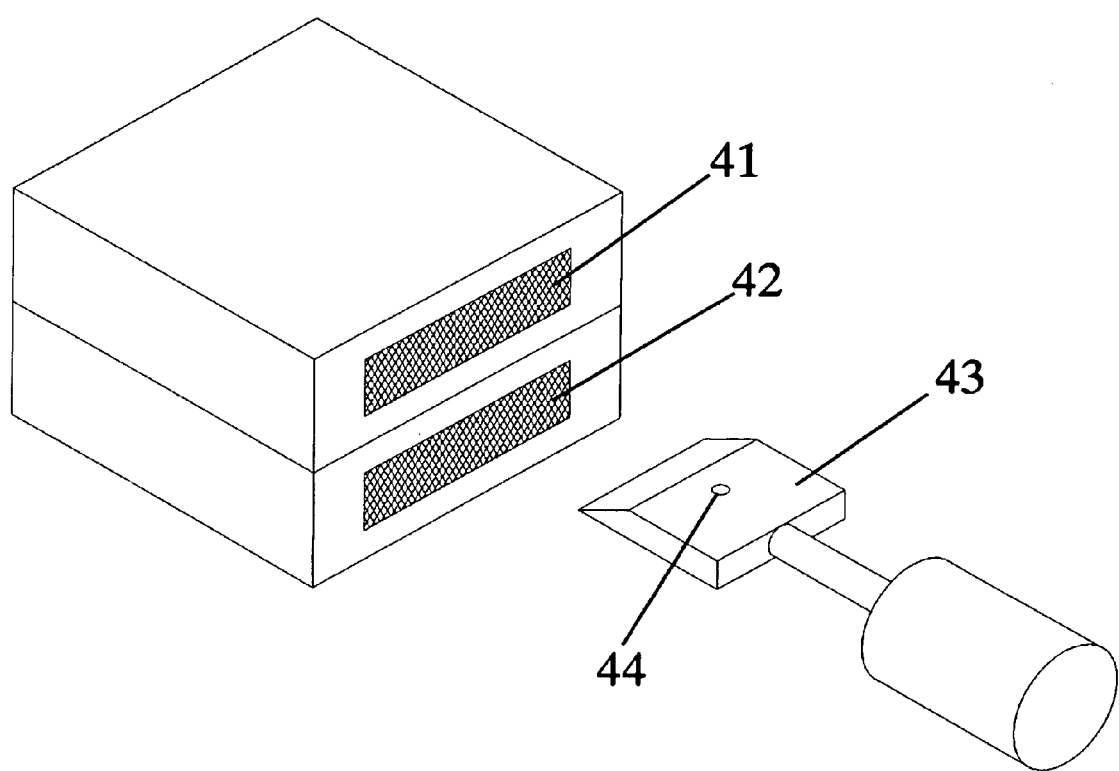
FIG. 4 a schematic diagram for a device where flat-shaped conductive liquid injector/discharger are used.

FIG. 4 is a schematic diagram for a casing where flat-shaped conductive liquid injector/discharger are used. Reference numerals 41 and 42 denote liquid injection/discharge openings communicable with the interior spaces, and reference numeral 43 denotes a flat-shaped conductive liquid injector/discharger. Reference numeral 44 denotes a liquid injection/discharge hole and liquid injection/discharge is conducted through this hole. Examples of the material for the conductive liquid injector/discharger include graphite, platinum, gold, and gold plated metals. The shapes of the conductive liquid injector/discharger include a comb-shaped arrange of plural conductive needles and a flat planar shape; however, a flat and wide shape shown in FIG. 4 is preferable for the purpose of making a specimen migrate uniformly into the gel immobilizing the probes of bio-related substances of the capillary array sheet.

Figure 5:
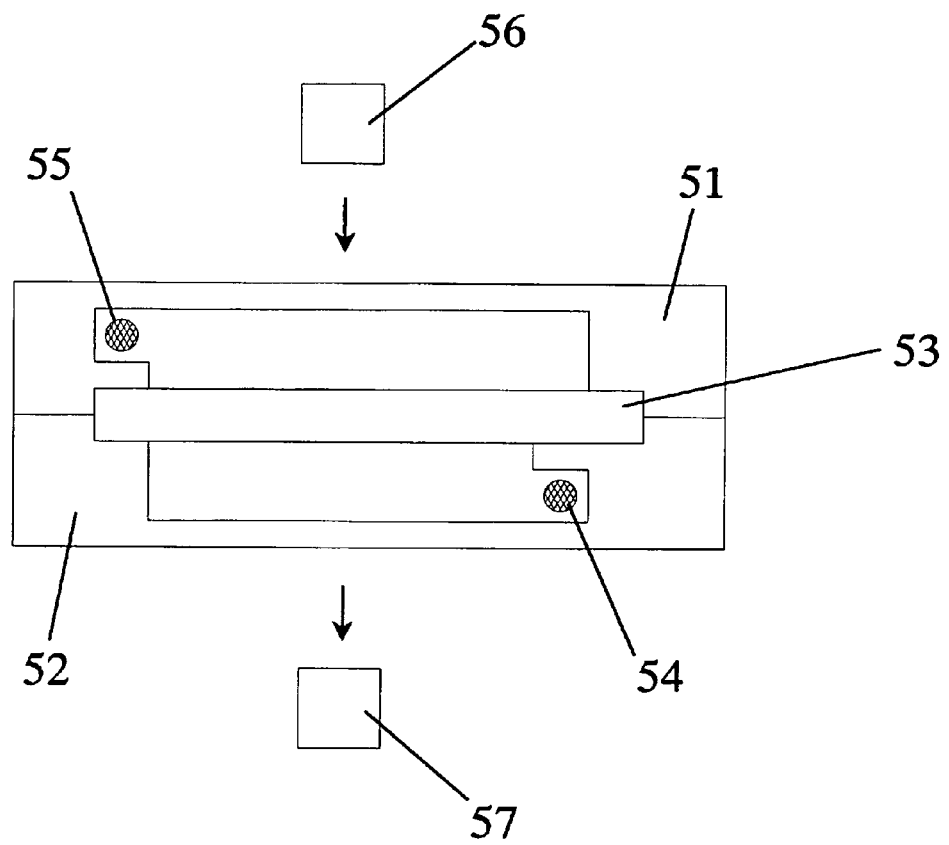
FIG. 5 is a schematic diagram illustrating a specimen detection method.

FIG. 5 is a schematic diagram illustrating a specimen detection method. If a specimen is fluorescence labeled, the specimen can be detected optically; as FIG. 5 shows, a light irradiator 56 irradiates light perpendicularly to the capillary array sheet through the casing component 51 and the fluorescence emitted from the specimen hybridized with the probes of bio-related substances immobilized in the gel in the capillary array sheet can be detected by a photodetector 57 such as a CCD camera. Additionally, if the matrix part of the capillary array sheet does not transmit light, the fluorescence radiated from the specimen can be detected with a high S/N. In this embodiment, reference numerals 54 and 55 denote conductive needles for liquid injection/discharge shown in FIG. 3. As FIG. 5 shows, if the needles are inserted into positions free from interfering with the light irradiation and fluorescence detection, the conditions of the specimens can be monitored in real time while conducting electrophoresis, washing and the like, and hence the hybridization reaction and the washing of the unnecessary specimens can be performed efficiently without fail, so that detection of the specimens with high precision can be made.

Figure 6:
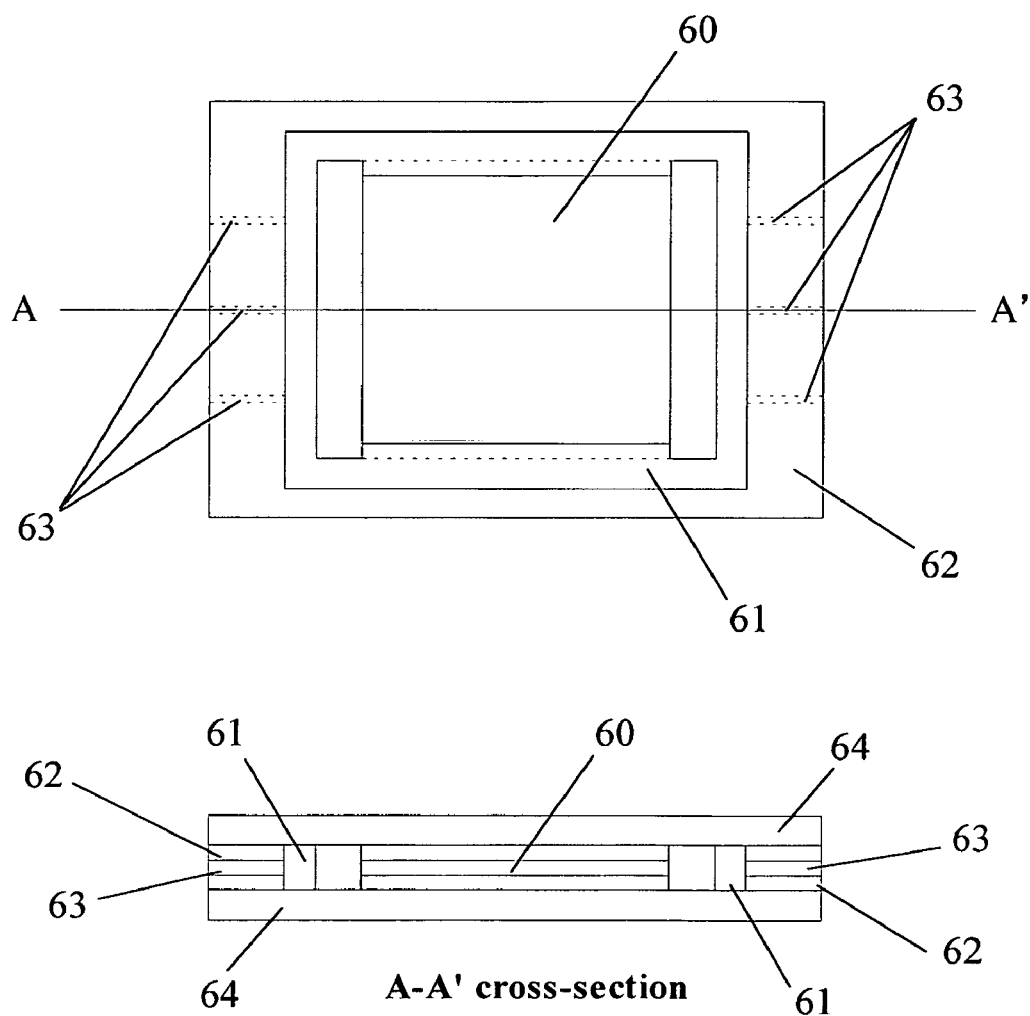
FIG. 6 is a schematic diagram of an electrophoretic device.

FIG. 6 is a schematic diagram of an electrophoretic device in which a capillary array sheet 60 fixed along the up-and-down direction by packing materials 61 is housed in a casing frame 62, the upper and lower surfaces of the sheet are covered with glass plates 64, and the interior of the packing materials 61 to which the capillary array sheet 60 is fixed is sealed. The packing materials 61 are preferably made of a soft rubber material or the like capable of sealing liquid and allowing the needle for liquid injection/discharge to be inserted. The casing frame 62 is provided with insertion holes 63 so that the needles for liquid injection/discharge can be inserted.

Figure 7:
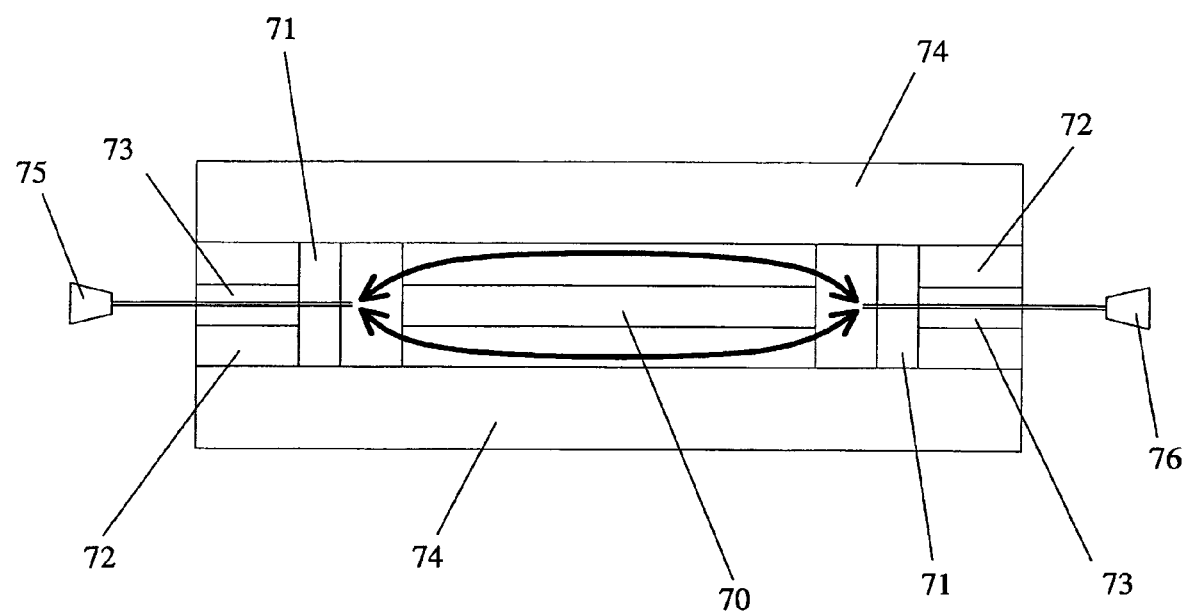
FIG. 7 is a schematic diagram illustrating a section of an electrophoretic device.

The liquid injection/discharge is conducted as shown in FIG. 7 in such a way that needles 75, 76 for liquid injection/discharge are inserted through insertion holes 73 arranged in a casing frame 72 to penetrate into the packing materials 71, and for example, while injecting liquid through the needle 75 for liquid injection/discharge, the liquid or the gas in the interior of the sealed space is discharged from the needle 76 for liquid injection/discharge. In this casing, if the liquid is injected from the lower side and discharged from the upper side, the sealed space can be filled with the liquid without leaving air bubbles.

If the sealed space is filled with a specimen solution, the specimens spontaneously diffuse to the surface and into the interior of the gel immobilizing the probes of bio-related substances in the capillary array sheet 70 and form hybrids with the probes. On the other hand, if the sealed space is filled with a specimen solution and additionally the specimen solution is injected and discharged alternately from the needles 75, 76 for liquid injection/discharge, the flow of liquid as indicated by the arrows in FIG. 7 is generated in the sealed space, so that the specimens can be circulated uniformly all over the whole sealed space, and hybridization small in positional unevenness is possible. Additionally, if a voltage is applied alternately to the needles 75, 76 for liquid injection/discharge, an electric field is generated in the sealed space as indicated by the arrows in FIG. 7, the specimens are made to migrate uniformly all over the whole space, accordingly the hybridization small in positional unevenness is made possible, and the hybridization further small in positional unevenness is made possible if combined with the circulation caused by the liquid flow.

Similarly, if the washing solution is alternately injected and discharged through the needles 75, 76 for liquid injection/discharge, the liquid flow is generated in the sealed space as indicated by the arrows in FIG. 7, and thus the unnecessary specimens not involved in hybridization formation can be removed from the surface and the interior of the electrophoretic carrier with the aid of the liquid flow. Additionally, if a voltage is applied alternately to the needles 75, 76 for liquid injection/discharge, the electric field is generated in the sealed space as indicated by the arrows in FIG. 7, and thus the unnecessary specimens not involved in hybridization formation can be removed from the surface and the interior of the electrophoretic carrier with the aid of electrophoresis, and a further efficient removal of the unnecessary specimens can be carried out if combined with the liquid flow.

Figure 8:
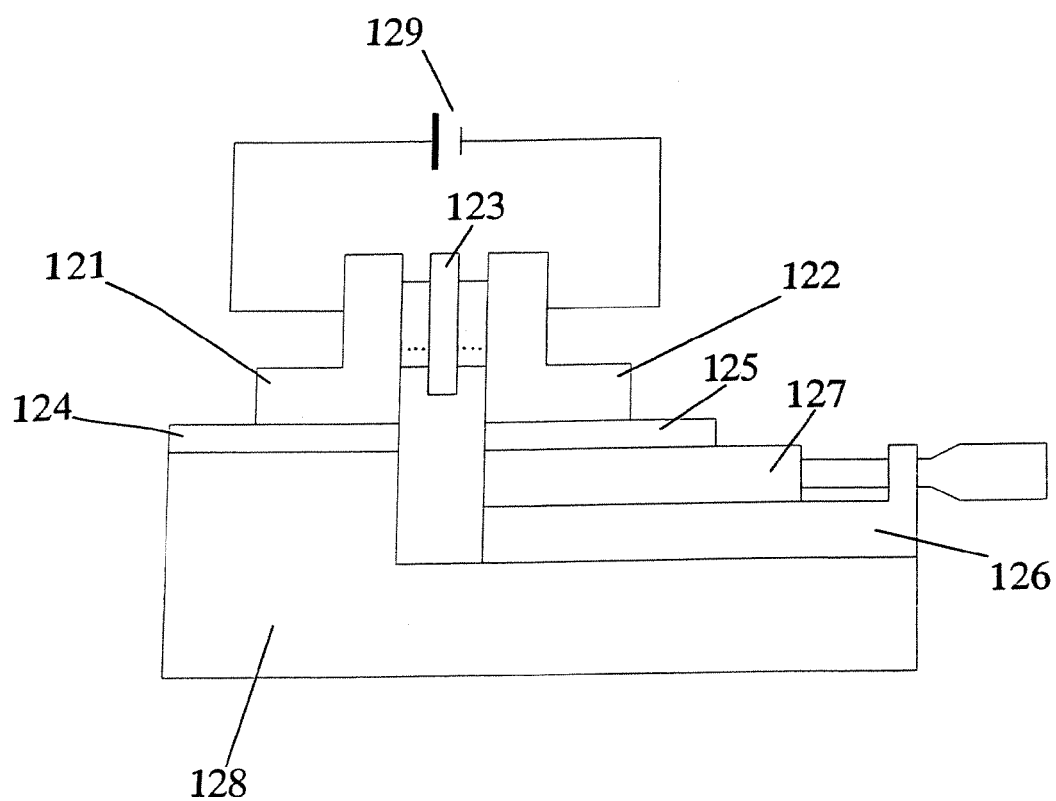
FIG. 8 is a schematic diagram illustrating an electrophoresis apparatus.

FIG. 8 is a schematic diagram illustrating an electrophoresis apparatus, showing a condition in which the capillary array sheet is sandwiched between the electrodes. The thickness of the capillary array sheet falls within the range from a few tens microns to the order of 1 mm. The area sizes usually used are squares of a few mm to a few cm per side. Reference numeral 128 denotes the base of the apparatus, 121, 122 denote electrodes, 124, 125 denote insulators, 123 denotes a capillary array sheet, 126 denotes a manual type movable stage, 127 denotes a movable carriage, and 129 denotes an electric power supply. The electrode 121 is fixed to the base 128 of the apparatus, being insulated by the insulator 124, while the electrode 122 is fixed onto the movable carriage 127, being insulated by the insulator 125, wherein carriage is on the movable stage 126 in turn fixed to the base 128. Thus, the electrode 122 is movable together with the movable carriage 127 of the movable stage 126. The spacing between the electrodes 121, 122 is widened by moving the movable carriage 127, the capillary array sheet 123 is inserted between the electrodes, and then the movable carriage 127 is moved to the reverse direction to narrow the spacing between the electrodes 121, 122, so that the capillary array sheet 123 can be sandwiched by the electrodes 121, 122 with an appropriate force exerted. In this way, a capillary array sheet of any optional thickness can be sandwiched between the electrodes.

The sandwiching structure in FIG. 8 is a configuration in which the capillary array sheet is used as a packing; if the packing effect of the capillary array sheet is poor, the capillary array sheet may be pressed with thin packings each inserted between the capillary array sheet and either of the electrodes. For the purpose of increasing the packing effect of the capillary array sheet, a relatively soft resin may be used for the matrix shown in FIG. 1.

Examples of the sandwiching structure other than the structure shown in FIG. 8 can include a structure in which the electrodes 121, 122 are grasped and fixed by using an insulating clamp and a structure in which the electrodes 121, 122 are screwed up similarly by using insulating screws.

Figure 9:
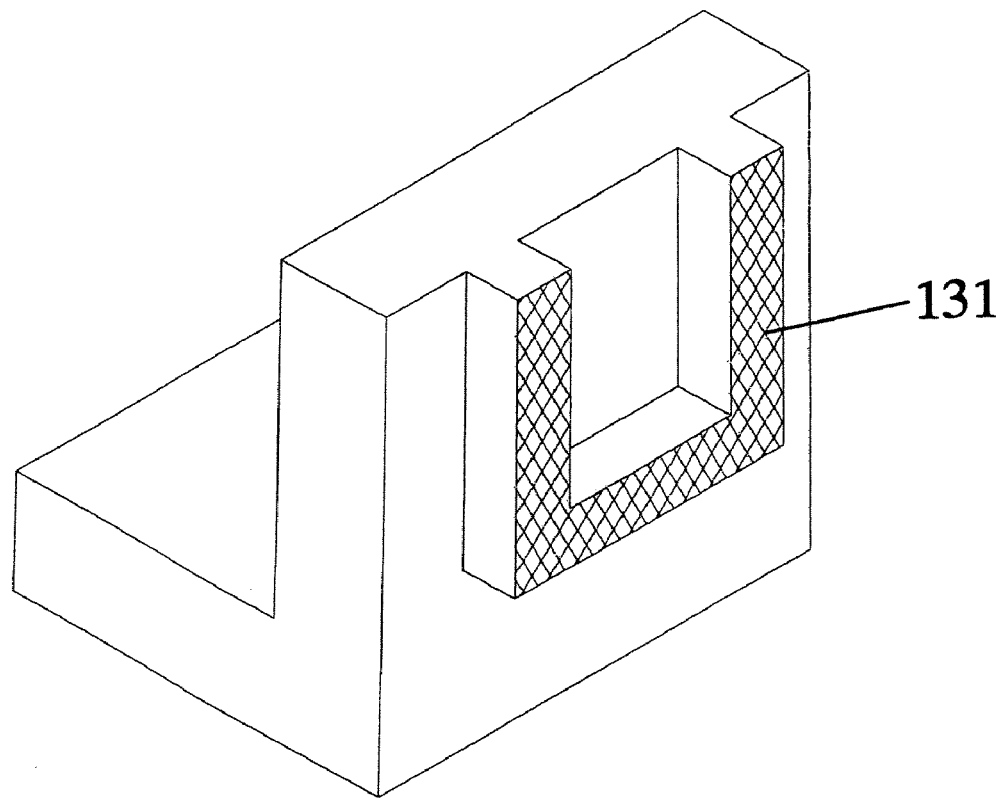
FIG. 9 is a perspective view of an electrode.

FIG. 9 is a perspective view of an electrode; when the electrode is used to sandwich the capillary array sheet, the shown surface of the electrode 131 and the matrix portion of the capillary array sheet closely contact each other to form a space between the electrode and the capillary array sheet. More specifically, the electrode has a structure in which a horseshoe-shaped portion is formed on a surface of the electrode, so that an electrolyte and specimens can be injected into the space to conduct electrophoresis by applying a voltage between the electrodes. When no horseshoe-shaped portion is formed on the electrode, by sandwiching as described above the capillary array sheet together with a packing of an appropriate thickness inserted between the capillary array sheet and the electrode, the space having a width corresponding to the packing thickness can be used as a liquid holding space.

Various electrode shapes are possible; by optimizing the shape of the surface 131 to be in close contact with the matrix portion of the capillary array sheet according to the area size, thickness and hardness of the capillary array sheet and sandwiching capillary array sheet between the electrodes with an appropriate force, a space free from liquid leaking can be formed between the electrode and the capillary array sheet. For example, in a capillary array sheet of 20×20 mm in area size and 0.5 mm in thickness formed with the matrix portion made of an urethane resin, the portion 131 to be in close contact with the matrix portion of the capillary array sheet is preferably flat and of the order of 1 to 2 mm in width. In this casing, even when the capillary array sheet has some unevenness in thickness, if the capillary array sheet is sandwiched with an appropriate force, a space free from liquid leakage can be formed between the electrode and the capillary array sheet.

Examples of the electrode material include graphite, platinum, gold and gold plated metals. Transparent electrodes may also be used. Additionally, if the electrode temperature is controlled by embedding heaters in electrodes or by making the interior of the electrodes hollow to allow a liquid at an arbitary temperature to flow thereinto from outside, hybridization, dehybridization, washing or the like can be efficiently carried out at optimal temperatures.

Figure 10:
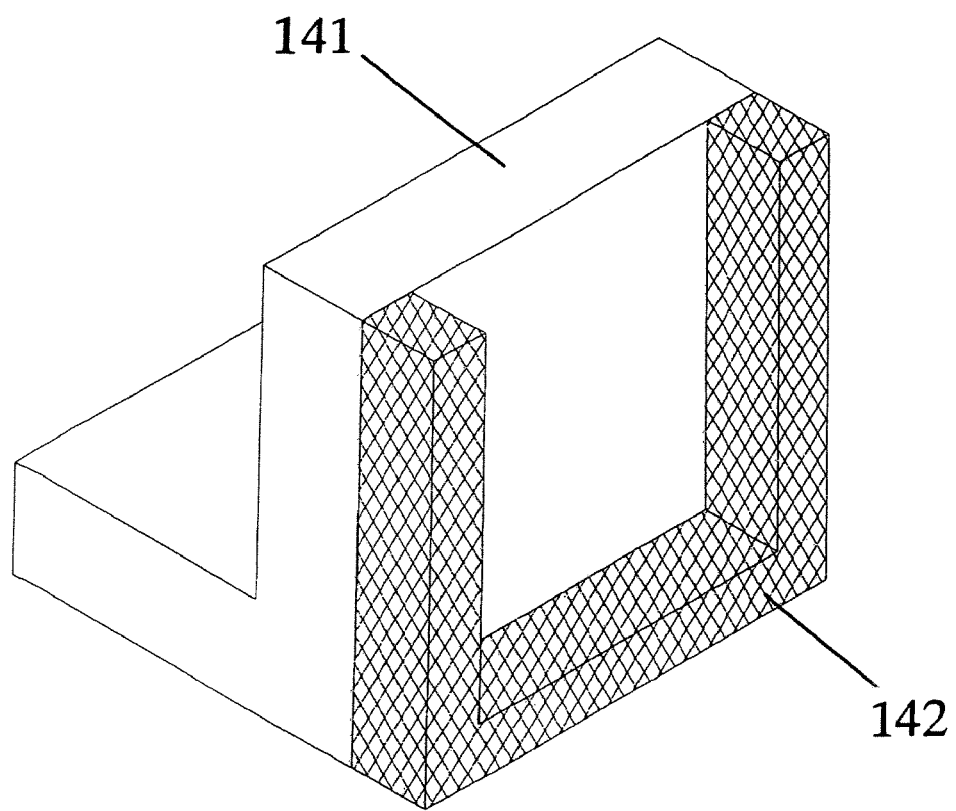
FIG. 10 is a perspective view of an electrode composed of a conductive portion and an insulating portion.

FIG. 10 is a perspective view of an electrode composed of a conductive portion 141 and an insulating portion 142.

In electrophoresis, sometimes gas bubbles are generated from electrodes by electrolysis. If the generated gas bubbles adhere to the spots immobilizing the polymer probes such as nucleic acids and the like, the migration behavior of the specimens on the spots with the gas bubbles adhered becomes at variance with the corresponding behavior on the other spots, therefore uniform hybridization or washing all over the whole spots can not be conducted, resulting in failure of accurate specimen detection. However, when the capillary array sheet is sandwiched vertically between a pair of the electrodes shown in FIG. 10, spaces each with opened upper side are formed between the electrodes and the capillary array sheet; the gas bubbles generated from the conductive portions of the electrodes go upward without adhering to the capillary array sheet, and are eventually discharged from the upper openings into the air.

In this embodiment, when at least one position on the electrode is provided with a liquid injection/discharge opening, even if the spaces between the electrodes and the capillary array sheet are sealed, the specimen, electrolyte and washing solution can be injected or discharged through the liquid injection/discharge opening; additionally, even if spaces with upper openings are formed between the electrodes and the capillary array sheet, the specimen, electrolyte and washing solution can be circulated, and hybridization or washing can be efficiently carried out.

Figure 11:
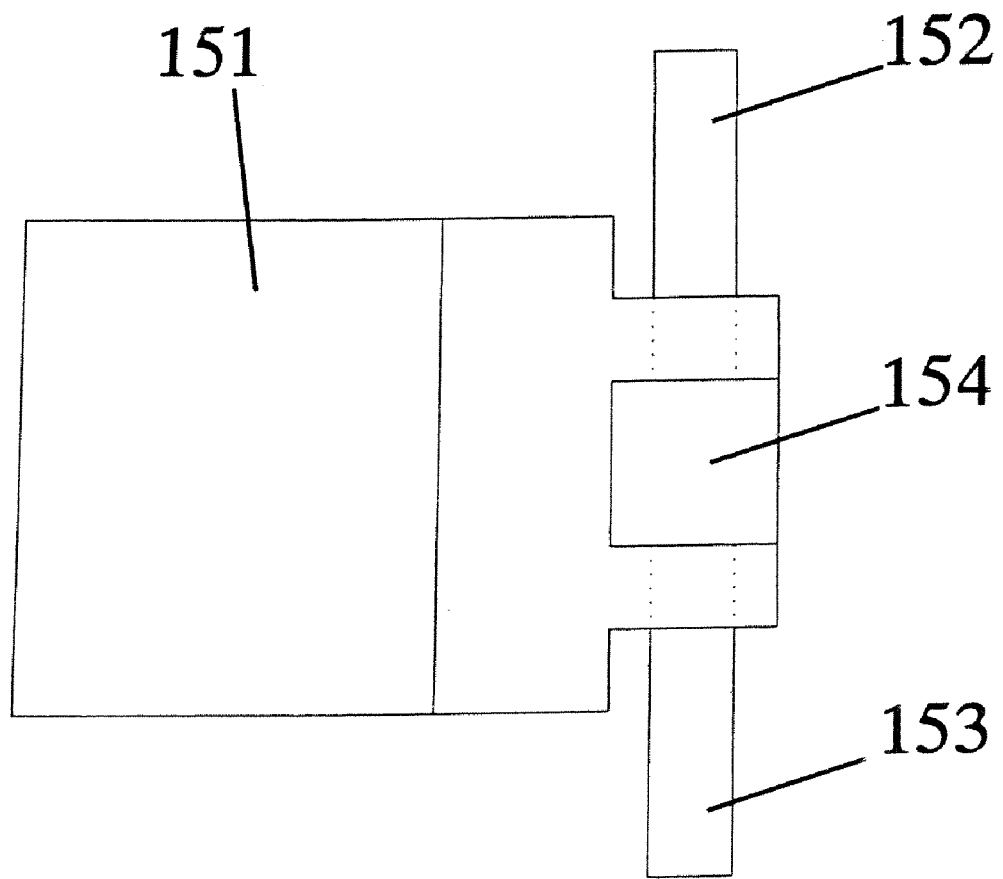
FIG. 11 is a schematic diagram illustrating an electrode having a liquid injection opening and a liquid discharge opening.

FIG. 11 is a top view of an electrode; an electrode 151 is provided with a liquid injection opening 152 and a liquid discharge opening 153. Through the liquid injection and discharge openings, the specimen, electrolyte and washing solution can be injected into and discharged from a space formed between the horseshoe-shaped portion 154 of the electrode and the capillary array sheet.

Figure 12:
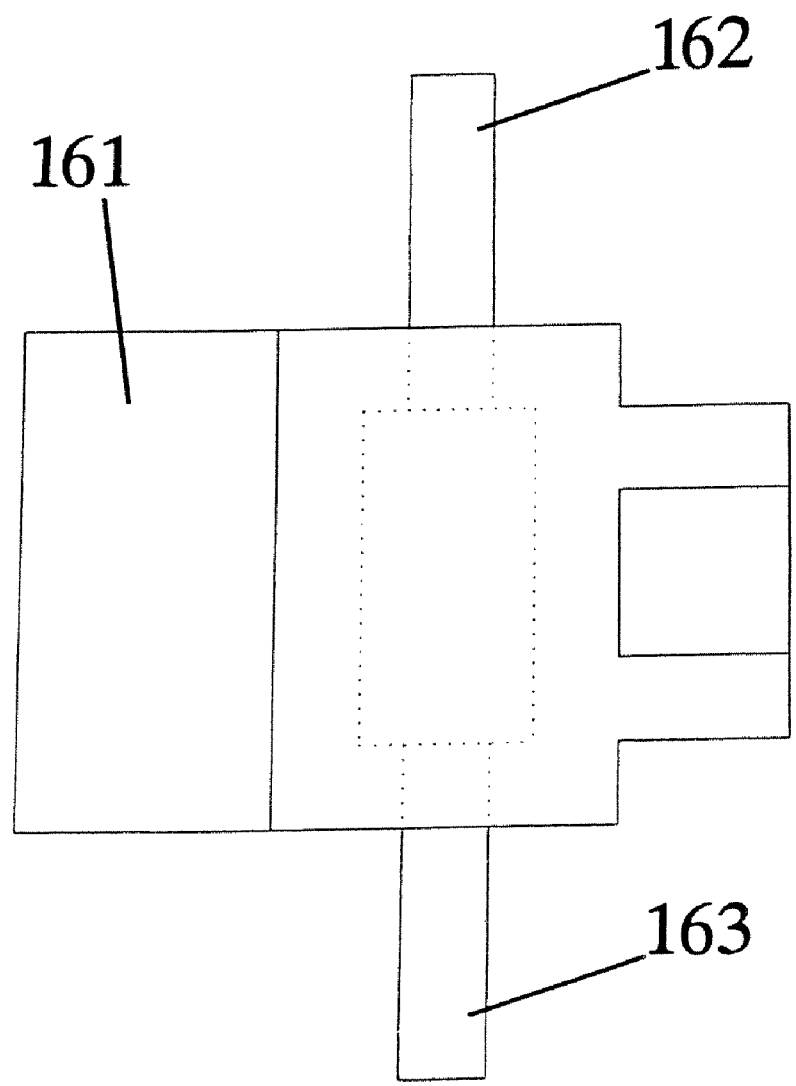
FIG. 12 is a schematic diagram illustrating a temperature controllable electrode.

FIG. 12 shows an example of a temperature controllable electrode. The interior of an electrode 161 makes a cavity, and a liquid at an arbitary temperature is circulated through an inlet/outlet 162 and 163 communicated with the internal cavity, so that the temperature of the electrode 161 can be controlled.

Figure 13:
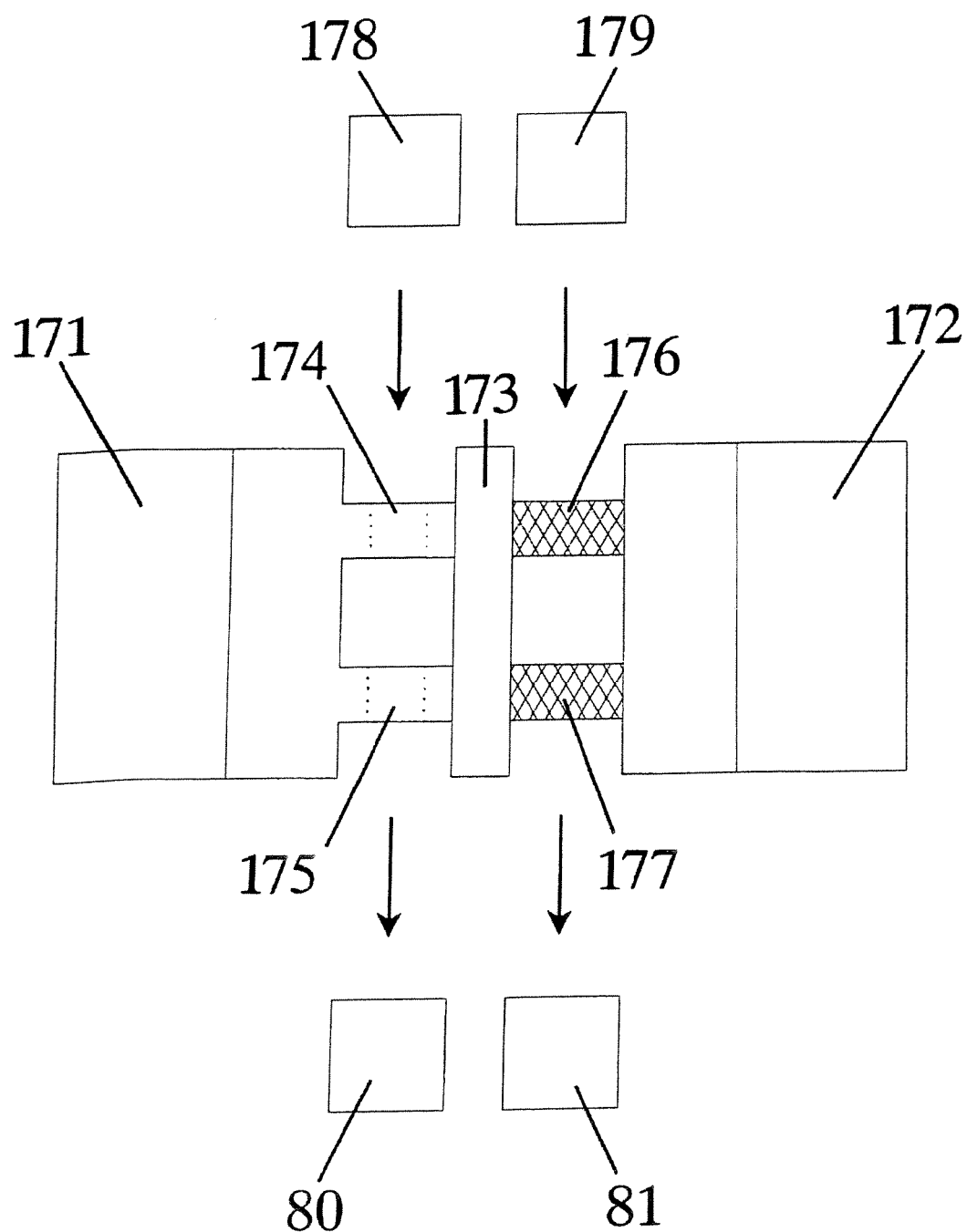
FIG. 13 is a schematic top view illustrating a condition in which a capillary array sheet is sandwiched between electrodes with window.

FIG. 13 is a schematic top view illustrating a condition in which a capillary array sheet is sandwiched between electrodes with window. Reference numeral 171 denotes an electrode, which is provided with windows 174, 175. Reference numeral 172 also denotes an electrode, which is an example in which the whole of each of portions 176, 177 is a window. Examples of the materials for the windows include transparent materials such as glass, acrylic resin and the like. Reference numeral 173 denotes a capillary array sheet, 178, 179 each denotes a light irradiator, and 80, 81 each denotes a photodetector. This figure shows an example in which both electrodes are provided with windows; however, only one of the electrodes may be provided with windows and the specimen concentrations in the liquid present in one side of the capillary array sheet may be detected.

The capillary array sheet detects a specimen on the basis of the fact that the particular specimen is bound to a probe immobilized on a particular spot on the capillary array sheet. For example, when by use of a capillary array sheet having the spots immobilizing 25 different types of probes, one type of specimen able to be bound to one type of the 25 types is to be detected, the capillary array sheet is sandwiched between a pair of electrodes, and the specimen is made to migrate by electrophoresis uniformly to the spots on the capillary array sheet; thus ¹/₂₅ of the specimen migrates to each of the spots, and the specimen is bound to the probe on one spot but the specimen passes through the other 24 spots without being bound to the probes on these spots. Thus, if the polarity of the electrodes is reversed, or if at least one position of each electrode is provided with a liquid injection/discharge opening and the specimen and electrolyte, separated by the capillary array sheet, are circulated through the liquid injection/discharge opening without changing the polarity of the electrodes, and additionally electrophoresis is repeatedly conducted, then the amount of the specimen bound to the probe is increased, so that the S/N of the detection can be enhanced.

On the other hand, for example, when various types and various sizes of nucleic acids are subjected to electrophoresis, because the electrophoresis behaviors of the respective nucleic acids are different from each other, if the polarity of the electrodes is reversed or the specimen and electrolyte are circulated at the stage where all of the short chain nucleic acids migrate into the gel but only part of the long chain nucleic acids migrate into the gel, the detection of the nucleic acids cannot possibly be carried out with good precision. Accordingly, if the electrophoresis conditions of the nucleic acids can be monitored in real time, reliable and efficient hybridization and washing of the unnecessary specimens can be carried out, so that a high precision detection of nucleic acids comes to be possible.

In this connection, if the specimens are fluorescence labeled, optical detection of the specimens becomes possible; as FIG. 13 shows, the light irradiators 178, 179 irradiate light, through the windows 174, 176 provided on the electrodes 171, 172, to the spaces between the electrodes 171, 172 and the capillary array sheet 173; the fluorescence radiated from the fluorescence labeled specimens present in the spaces between the electrodes 171, 172 and the capillary array sheet 173 are detected by the photodetectors 80, 81 through the windows 175, 177 provided on the electrodes 171, 172; and by following this way, the electrophoresis behaviors of the specimens can be monitored in real time. Additionally, on the basis of the fluorescence intensities monitored, the reversal of the applied voltage, the alteration of the applied voltage value, the circulation of the specimens and electrolyte and the like can be controlled; and therewith efficient and reliable hybridization and washing of the unnecessary specimens can be carried out, so that a detection of specimens with high precision comes to be possible. Additionally, the specimens and electrolyte are led outward through transparent glass tubes and the like from the liquid injection/discharge opening of the electrode and are similarly irradiated with light, thereby enabling to carry out the real time monitoring of the electrophoresis behaviors of the specimens.

In FIG. 13, the light irradiators 178, 179 and the photodetectors 80, 81 are respectively arranged on the straight lines, but the light irradiators 178, 179 and the photodetectors 80, 81 may be respectively arranged on the lines perpendicular to each other. For example, more specifically with reference to FIG. 13, the photodetectors 80, 81 are arranged above or below the plane of the Fig., windows are arranged on the upper openings of the spaces formed between the electrodes 171, 172 and the biochip 173 or on the bottoms of the electrodes 171, 172, and the fluorescence radiated from the fluorescence labeled specimens may be detected through the windows thus provided. Additionally, the windows 174, 175, 176, 177 arranged on the electrodes 171, 172, the light irradiators 178, 179, and the photodetectors 80, 81 may be connected with optical fibers to each other.

Figure 14:
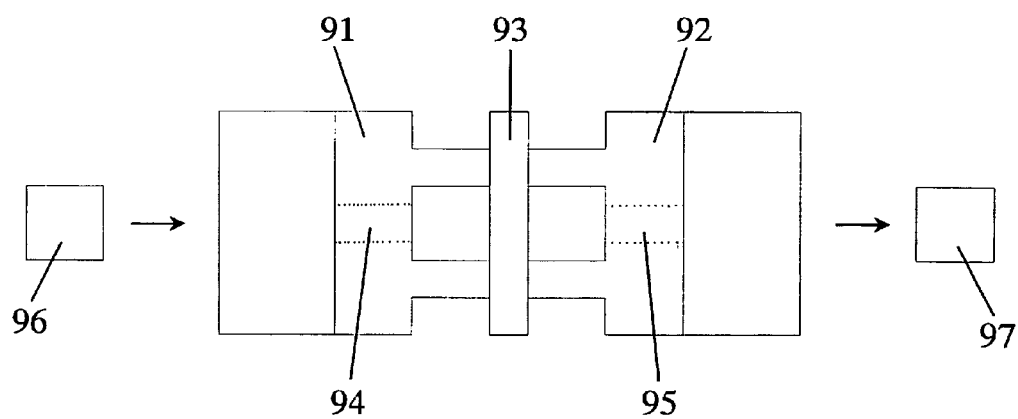
FIG. 14 is a schematic top view illustrating a condition in which a capillary array sheet is sandwiched between electrodes with window.

Additionally, in FIG. 13, light is irradiated such that the light direction is parallel to the surface of the capillary array sheet. However, as FIG. 14 shows, a window 94 is provided on an electrode 91 along a direction perpendicular to the surface of the capillary array sheet; light is irradiated from a light irradiator 96 through the window 94 to the surface of the capillary array sheet 93; the fluorescence radiated from the fluorescence labeled specimens present in the gel in the capillary array sheet 93 is detected by a photodetector 97 such as a CCD through a window 95 provided on a facing electrode 92; and by following this way, detecting the dropping of the gel in the capillary array sheet, detecting the bubble adhesion, and monitoring in real time of the electrophoresis behaviors of the specimens in the gel in the capillary array sheet become possible. In this embodiment, if the matrix of the capillary array sheet and the hollow fibers holding the gel do not transmit light, a high S/N detection of fluorescence can be made.

BEST MODE FOR CARRYING OUT THE INVENTION

Specific description will be made on the present invention on the basis of examples, but the scope of the present invention is not limited to the scope of these examples.

Example 1

(1) Preparation of the Capillary Array Sheet

By using 2 perforated plates of 0.1 mm in thickness each having 25 holes of 0.32 mm in diameter arranged in the central portion thereof at intervals of 0.42 mm in a 5×5 grid pattern, all the holes in the 2 superposed perforated plates were passed through by hollow fibers (outside diameter: 0.25 mm; inside diameter: 0.18 mm; length: 500 mm) made of polymethyl methacrylate. Thereafter, the spacing between the 2 perforated plates was widened to 50 mm, and a polyurethane resin colored with carbon black was poured into the space between the fibers and the fibers were embedded in a rectangular column of 50 mm long and 20 mm square cross section. Thus, a hollow fiber arrangement body was obtained with both end parts of the hollow fibers not fixed with resin. In the center of 20 mm square cross section of the square pole, there is an area 2.0 mm per side, having 25 hollow fibers arranged.

Only a gel precursor solution was charged in the 22 hollow fibers in the obtained hollow fiber arrangement body. A gel precursor solution containing a nucleic acid probe A of 40 bases was charged in the remaining 3 hollow fibers, and was allowed to be polymerized. Thereafter, by using a microtome, the hollow fiber arrangement body was cut perpendicularly to the fiber axis into 0.5 mm thick thin slices and thus capillary array sheets were obtained.

(2) Detection of the Specimens

An capillary array sheet obtained above was placed in a casing made of acrylic resin shown in FIG. 3. In this case, as FIG. 2 shows, the capillary array sheet was sandwiched between the casing parts by applying an appropriate pressure, and the casing parts were bonded and fixed to each other with an adhesive. The capillary array sheet may be trimmed so that the sheet may be sandwiched between the casing parts. The spaces isolated by the capillary array sheet sandwiched between the casing parts were 10 mm long, 10 mm wide and 1 mm high. For the purpose of preservation, the spaces were filled with a sterilized water through the liquid injection/discharge openings by using a liquid injector/discharger, shown in FIG. 3, which was a gold plated, stainless steel hollow tube of 0.3 mm in inside diameter. After filled with the sterilized water, the liquid injection/discharge openings were closed with rubber lids.

In the next place, for the purpose of detecting specimens, 2 liquid injectors/dischargers were inserted through the liquid injection/discharge opening into one of the spaces isolated by the capillary array sheet. While discharging the filled sterilized water by use of one of the liquid injector/discharger, 0.5×TBE, 120 fmol of an nucleic acid specimen a of 40 bases complementarily to be bonded to the nucleic acid probe A, labeled with the Cy5 dye, and 120 fmol of a nucleic acid specimen b of 40 bases complementarily not to be bonded to the nucleic acid probe A, labeled with the Cy3 dye, were injected through the other liquid injector/discharger.

Also into the other space isolated by the capillary array sheet, 2 liquid injectors/dischargers were inserted through the liquid injection/discharge openings. While discharging the filled sterilized water by use of one of the liquid injector/discharger, only 0.5×TBE was injected through the other liquid injector/discharger. After the discharge and injection operations, the liquid injectors/dischargers for the space in which the specimens were injected were used as the negative electrode, the liquid injectors/dischargers for the space in which only the electrolyte was injected were used as the positive electrode, and a voltage of 0.5 V was applied between the electrodes to carried out electrophoresis for 3 hours.

After completion of the electrophoresis, once again the sterilized water was filled through the liquid injector/discharger, the capillary array sheet was observed by use of a fluorescence microscope through the casing made of acrylic resin. Consequently, the fluorescence emitted from the Cy5 dye was able to be detected only for the 3 spots of the capillary array sheet where the nucleic acid probe A was immobilized. The fluorescence emitted from the Cy3 dye was not observed from any spot.

Example 2

The capillary array sheet obtained in Example 1 was placed in a casing made of acrylic resin to form a device, the electrolyte and the fluorescence labeled nucleic acid specimen were similarly injected through the liquid injectors/dischargers, and electrophoresis was conducted similarly for 3 hours. Thereafter, while applying a voltage, 0.5×TBE as a washing solution was injected and discharged through the liquid injector/discharger to perform washing for 30 minutes.

After completion of the washing, once again the sterilized water was filled through the liquid injector/discharger, the capillary array sheet was observed by use of a fluorescence microscope through the casing made of acrylic resin. Consequently, the fluorescence emitted from the Cy5 dye was able to be detected only for the 3 spots of the capillary array sheet where the nucleic acid probe A was immobilized. The fluorescence emitted from the Cy3 dye was not observed from any spot. Additionally, the S/N of the intensity of the fluorescence emitted from the Cy5 dye, detected only from the 3 spots where the nucleic acid probe A was immobilized, was found to be improved by a factor of about 3 as compared to that detected in Example 1.

Example 3

The capillary array sheet obtained in Example 1 was sandwiched vertically, with the aid of the sandwiching structure shown in FIG. 8, between a pair of electrodes made of gold plated stainless steel, as shown in FIG. 9, in which the dimension of the horseshoe-shaped portion was 10 mm wide and 15 mm high, and the depth of the horseshoe-shaped portion is 1 mm; thus spaces with upper openings were formed between the electrodes and the capillary array sheet. In this case, each of the spaces between the electrodes and the capillary array sheet, as viewed from above, was 10 mm wide, 1 mm high and 15 mm deep.

Into the space between the electrode of the negative electrode section and the capillary array sheet, from the upper opening thereof, 120 μl of 0.5×TBE, 120 fmol of an nucleic acid specimen a of 40 bases complementarily to be bonded to the nucleic acid probe A, labeled with the Cy5 dye, and 120 fmol of a nucleic acid specimen b of 40 bases complementarily not to be bonded to the nucleic acid probe A, labeled with the Cy3 dye, were injected as the electrolyte; into the space between the electrode of the negative electrode section and the capillary array sheet, from the upper opening thereof, only 120 μl of 0.5×TBE was injected as the electrolyte from the upper opening; and a voltage of 0.5 V was applied between the electrodes to conduct electrophoresis for 3 hours.

After completion of the electrophoresis, as a result of the fluorescence microscopic observation, the fluorescence emitted from the Cy5 dye was able to be detected only for the 3 spots of the capillary array sheet where the nucleic acid probe A was immobilized. The fluorescence emitted from the Cy3 dye was not observed from any spot.

Example 4

Similarly to Example 3, the capillary array sheet obtained in Example 1 was sandwiched vertically, with the aid of the sandwiching structure shown in FIG. 8, between a pair of electrodes made of gold plated stainless steel having a window made of acrylic resin, in which the dimension of the horseshoe-shaped portion was 10 mm wide and 15 mm high, and the depth of the horseshoe-shaped portion is 1 mm; thus spaces with upper openings were formed between the electrodes and the capillary array sheet; into the space between the electrode of the negative electrode section and the capillary array sheet, from the upper opening thereof, 120 µl of 0.5×TBE and 120 fmol of an nucleic acid specimen a of 40 bases complementarily to be bonded to the nucleic acid probe A, labeled with the Cy5 dye, were injected as the electrolyte; into the space between the electrode of the positive electrode section and the capillary array sheet, from the upper opening thereof, only 120 µl of 0.5×TBE was injected as the electrolyte; and a voltage of 0.5 V was applied between the electrodes to conduct electrophoresis, according to the configuration as shown in FIG. 13 (however, the photodetectors corresponding to 80, 81 were arranged at some upper space positions perpendicularly away from the irradiating light direction), while monitoring the intensity of the fluorescence emitted from the specimens present in the space between the electrode of the positive electrode section and the capillary array sheet and in the space between the electrode of the negative electrode section and the capillary array sheet. As the light irradiator, a 633 nm laser was used, and the detection of the fluorescence intensity was carried out in such a way that the fluorescence radiated from the upper opening between the electrode and the capillary array sheet was detected by use of a photosensor through an optical filter. From the fluorescence intensity variation, it was able to be confirmed that in 1.5 hours, the specimen present in the space between the electrode in the negative electrode section and the capillary array sheet migrated into the interior of the gel in the capillary array sheet and into the space between the electrode of the positive electrode section and the capillary array sheet. Then, additionally electrophoresis was conducted with the reversed polarity of the electrodes, and consequently, the specimen that had migrated was found to migrate in 1 hour to the space between the opposite electrode and the capillary array sheet.

At this stage, the capillary array sheet was taken out, and subjected to the fluorescence microscopic observation; consequently, the fluorescence emitted from the Cy5 dye was able to be detected only for the 3 spots of the capillary array sheet where the nucleic acid probe A was immobilized; and the detected fluorescence intensity was about twice as that detected in Example 3.

All the publications, patents, and applications for patent cited in the present specification are included as references as they are in the present specification.

INDUSTRIAL APPLICABILITY

By housing a capillary array sheet in a casing in which electrophoresis, hybridization, washing and detection can be carried out, there are provided an electrophoretic device, an electrophoresis apparatus, an electrophoretic method and a specimen detection method, which are inexpensive and compatible with mass production, for detecting the specimens of bio-related substances such as nucleic acids, proteins, polypeptides and polysaccharide. Additionally, the contamination of the chips and the dehydration of the gel during preservation and transportation can be prevented. Furthermore, according to the present invention, by the use of capillary array sheets, it becomes possible to efficiently and highly precisely detect biopolymer specimens such as nucleic acids.

The invention claimed is:

1. An electrophoresis apparatus, comprising:
   an electrophoretic carrier having one of a plurality of sizes, and formed of a capillary array sheet in which a polymer gel having probes immobilized thereto is held in the hollow portions of the capillaries;
   a pair of electrodes configured to sandwich therebetween the electrophoretic carrier; and
   a cavity provided between the sandwiched electrophoretic carrier and the respective electrodes, and configured to hold a liquid;
   wherein one electrode of the pair of electrodes is configured to be moved closer to and away from the second electrode to receive the electrophoretic carrier based on its size, the electrodes include horseshoe-shaped portions, and the horseshoe shaped portions define the cavity.

2. The electrophoresis apparatus according to claim 1 comprising, on the electrodes, at least one liquid injection/discharge opening communicable with the cavity.

3. The electrophoresis apparatus according to claim 1 comprising at least one light transmitting window on the electrodes.

4. An electrophoretic method, comprising:
   conducting electrophoresis using the electrophoretic apparatus according to claim 3 while specimens are being detected optically.

5. The electrophoresis apparatus according to claim 1, wherein the electrodes are temperature controllable.

* * * * *